US00PP26787P2

(12) United States Plant Patent
Beekenkamp

(10) Patent No.: US PP26,787 P2
(45) Date of Patent: May 31, 2016

(54) ***CAMPANULA* PLANT NAMED 'BKPCMPST'**

(50) Latin Name: *Campanula portenschlagiana*
Varietal Denomination: Bkpcmpst

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 14/121,883

(22) Filed: Oct. 31, 2014

(51) Int. Cl.
*A01H 5/02* (2006.01)

(52) U.S. Cl.
USPC ..... Plt./414

(58) Field of Classification Search
USPC ..... Plt./414
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Campanula* plant named 'Bkpcmpst' characterized by its compact, upright to outwardly spreading plant habit; freely branching habit; early and freely flowering habit; campanulate-shaped flowers with white-colored petals; and good garden performance.

2 Drawing Sheets

Botanical designation: *Campanula portenschlagiana.*
Cultivar denomination: 'BKPCMPST'.

BACKGROUND OF THE INVENTION

The present invention relates to a new and distinct cultivar of *Campanula* plant, botanically known as *Campanula portenschlagiana,* commonly known as Dalmatian Bellflower and hereinafter referred to by the name 'Bkpcmpst'.

The new *Campanula* is a product of a planned breeding program conducted by the Inventor in Maasdijk, The Netherlands. The objective of the breeding program is to create new freely flowering *Campanula* plants with attractive flowers and good interior and garden performance.

The new *Campanula* plant originated from a cross-pollination conducted by the Inventor in Maasdijk, The Netherlands in May, 2011 of a proprietary selection of *Campanula portenschlagiana* identified as code number 4401230, not patented, as the female, or seed, parent with a proprietary selection of *Campanula portenschlagiana* identified as code number 4401193, not patented, as the male, or pollen, parent. The new *Campanula* plant was discovered and selected by the Inventor as a single flowering plant from within the progeny of the stated cross-pollination grown in a controlled outdoor nursery in Maasdijk, The Netherlands in May, 2012.

Asexual reproduction of the new *Campanula* plant by terminal cuttings in Maasdijk, The Netherlands, since January, 2013 has shown that the unique features of this new *Campanula* plant are stable and reproduced true to type in successive generations.

SUMMARY OF THE INVENTION

Plants of the new *Campanula* have not been observed under all possible combinations of environmental conditions and Cultural practices. The phenotype may vary somewhat with variations in environmental conditions such as temperature and light intensity without, however, any variance in genotype.

The following traits have been repeatedly observed and are determined to be the unique characteristics of 'Bkpcmpst'. These characteristics in combination distinguish 'Bkpcmpst' as a new and distinct *Campanula* plant:

1. Compact, upright to outwardly spreading plant habit.
2. Freely branching habit.
3. Early and freely flowering habit.
4. Campanulate-shaped flowers with white-colored petals.
5. Good garden performance.

Plants of the new *Campanula* differ from plants of the female parent selection in the following characteristics:

1. Plants of the new *Campanula* flower earlier than plants of the female parent selection.
2. Plants of the new *Campanula* have flatter flowers than plants of the female parent selection.
3. Plants of the new *Campanula* and the female parent selection differ in flower color as plants of the female parent selection have light violet-colored flowers.

Plants of the new *Campanula* differ from plants of the male parent selection in the following characteristics:

1. Plants of the new *Campanula* have larger and lighter green-colored leaves than plants of the male parent selection.
2. Plants of the new *Campanula* have smaller flowers than plants of the male parent selection.

Plants of the new *Campanula* can be compared to plants of *Campanula* 'Spring Bell White', not patented. In side-by-side comparisons, plants of the new *Campanula* differ primarily from plants of 'Spring Bell White' in the following characteristics:

1. Plants of the new *Campanula* are more compact than plants of 'Spring Bell White'.
2. Plants of the new *Campanula* flower earlier than plants of 'Spring Bell White'.
3. Plants of the new *Campanula* produce new flowers above the older flowers whereas plants of 'Spring Bell White' produce new and old flowers at the same level.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the colors of the new *Campanula* plant.

The photograph on the first sheet is a side perspective view of a typical flowering plant of 'Bkpcmpst' grown in a container.

The photograph on the second sheet is a close-up view of a typical flowering plant of 'Bkpcmpst'.

DETAILED BOTANICAL DESCRIPTION

Plants used for the aforementioned photographs and following description were grown in 12-cm containers during the summer in a glass-covered greenhouse in Maasdijk, The Netherlands and under cultural practices typical of commercial production conditions. During the production of the plants, day temperatures ranged from 15° C. to 19° C. and night temperatures ranged from 14° C. to 16° C. Plants were 13.5 weeks old when the photographs and description were taken. In the following description, color references are made to The Royal Horticultural Society Colour Chart, 2007 Edition, except where general terms of ordinary dictionary significance are used.

Botanical classification: *Campanula portenschlagiana* 'Bkpcmpst'.

Parentage:

*Female, or seed, parent*.—Proprietary selection of *Campanula portenschlagiana* identified as code number 4401230, not patented.

*Male, or pollen, parent*.—Proprietary selection of *Campanula portenschlagiana* identified as code number 4401193, not patented.

Propagation:

*Type*.—By terminal cuttings.

*Time to initiate roots, summer and winter*.—About two weeks at temperatures about 19° C. to 20° C.

*Time to produce a rooted young plant, summer and winter*.—About three weeks at temperatures about 19° C. to 20° C.

*Root description*.—Medium in thickness, fibrous; white in color.

*Rooting habit*.—Moderately freely branching; medium density.

Plant description:

*Plant and growth habit*.—Herbaceous perennial; compact, upright to outwardly spreading plant habit; freely branching habit with about 36 branches developing per plant; moderately vigorous growth habit.

*Plant height*.—About 14.4 cm.

*Plant width*.—About 28.1 cm.

*Lateral branch description*.—Aspect: Upright to prostrate, ranging from about 5° to 90° from vertical. Length: About 10.2 cm. Diameter: About 2 mm. Internode length: About 1.1 cm. Strength: Moderately weak. Texture: Smooth, glabrous. Color: Close to 143B.

Leaf description:

*Arrangement*.—Alternate, simple.

*Length*.—About 2.2 cm.

*Width*.—About 1.8 cm.

*Shape*.—Cordate to deltoid.

*Apex*.—Acute.

*Base*.—Reniform to truncate.

*Margin*.—Coarsely dentate.

*Texture, upper surface*.—Smooth, glabrous.

*Texture, lower surface*.—Moderately pubescent.

*Venation pattern*.—Pinnate.

*Color*.—Developing and fully expanded leaves, upper surface: Close to N137C; venation, close to 138A. Developing and fully expanded leaves, lower surface: Close to 138B; venation, close to 138A.

*Petioles*.—Length, lower leaves: About 2.3 cm. Diameter, lower leaves: About 1.5 mm. Texture, upper and lower surfaces: Smooth, glabrous. Color, upper and lower surfaces: Close to 143B to 143C.

Flower description:

*Flower arrangement and shape*.—Single campanulate flowers arranged in axillary and terminal cymes; flowers face upright to outwardly; freely flowering habit with about 17 flowers developing per terminal inflorescence, about six inflorescences developing per axillary inflorescence and about 1,250 flowers per plant developing during the flowering season.

*Natural flowering season*.—Early flowering habit; plants begin flowering about 13 weeks after planting; in the garden, flowering continuous from late May to late August in The Netherlands.

*Flower longevity on the plant*.—About 18 days; flowers persistent.

*Fragrance*.—Faint, pleasant.

*Inflorescence height*.—About 5.4 cm.

*Inflorescence diameter*.—About 7 cm.

*Flower buds*.—Length: About 1.2 cm. Diameter: About 1 cm. Shape: Obovate. Color: Developing sepals (outer surface), close to 143B to 143C; developing petals, close to 150D.

*Flower diameter*.—About 3.2 cm.

*Flower length* (*height*).—About 1.8 cm.

*Petals*.—Arrangement: Five, or occasionally six, in a single whorl; lower 40% of petal length fused. Length: About 1.7 cm. Width, free part of the petal: About 9 mm. Shape: Ovate. Apex: Apiculate. Margin: Entire. Texture, upper and lower surfaces: Smooth, glabrous. Color: When opening, upper surface: Close to NN155D. When opening, lower surface: Close to NN155C; towards the apex, close to NN155A. Fully opened, upper and lower surfaces: Close to NN155D; color does not change with development.

*Sepals*.—Arrangement: Five, or occasionally six, in a single campanulate whorl; lower 20% of sepals fused. Length: About 9 mm. Width, base of free part of the sepal: About 1.5 mm. Shape: Lanceolate. Apex: Narrowly acute. Margin: Entire. Texture, upper and lower surfaces: Smooth, glabrous. Color: When developing, upper surface: Close to 143C. When developing, lower surface: Close to 143B to 143C. Fully developed, upper surface: Close to 143C. Fully developed, lower surface: Close to 143B.

*Peduncles*.—Length: About 3.2 cm. Diameter: About 1 mm. Aspect: Terminal inflorescences, upright; axillary inflorescences, about 40° from stem axis. Strength: Moderately weak. Texture: Smooth, glabrous. Color: Close to 143B.

*Pedicels*.—Length: About 8 mm. Diameter: About 0.75 mm. Aspect: About 40° from peduncle axis. Strength: Moderately weak. Texture: Smooth, glabrous. Color: Close to 143B.

*Reproductive organs*.—Stamens: Quantity per flower: Five. Filament length: About 1 mm. Filament color: Close to NN155D. Anther length: About 3 mm. Anther shape: Lanceolate. Anther color: Close to 4C. Pollen amount: Moderate. Pollen color: Close to 4D. Pistils: Quantity per flower: One. Pistil length: About 1.3 cm. Stigma shape: Decurrent. Stigma color: Close to 149D. Style length: About 1.1 cm. Style color: Close to 149D; towards the base, close to 157D. Ovary color: Close to 143C.

*Seeds and fruits*.—Seed and fruit production have not been observed on plants of the new *Campanula*.

Disease & pest resistance: Plants of the new *Campanula* have not been observed to be resistant to pathogens and pests common to *Campanula* plants.

Garden performance: Plants of the new *Campanula* have exhibited good tolerance to rain, wind and temperatures ranging from about −5° C. to about 30° C.

It is claimed:

1. A new and distinct *Campanula* plant named 'Bkpcmpst' as illustrated and described.

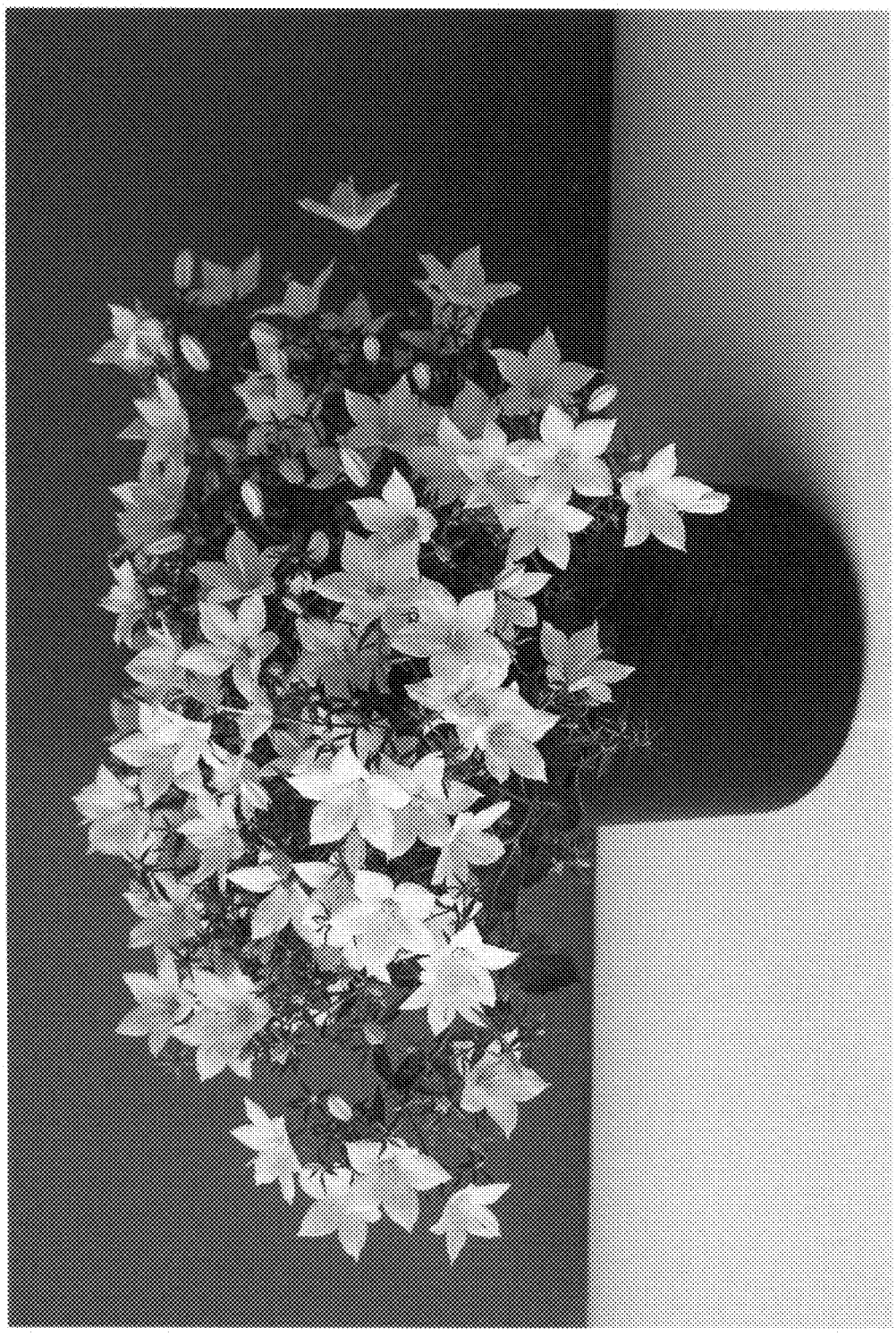

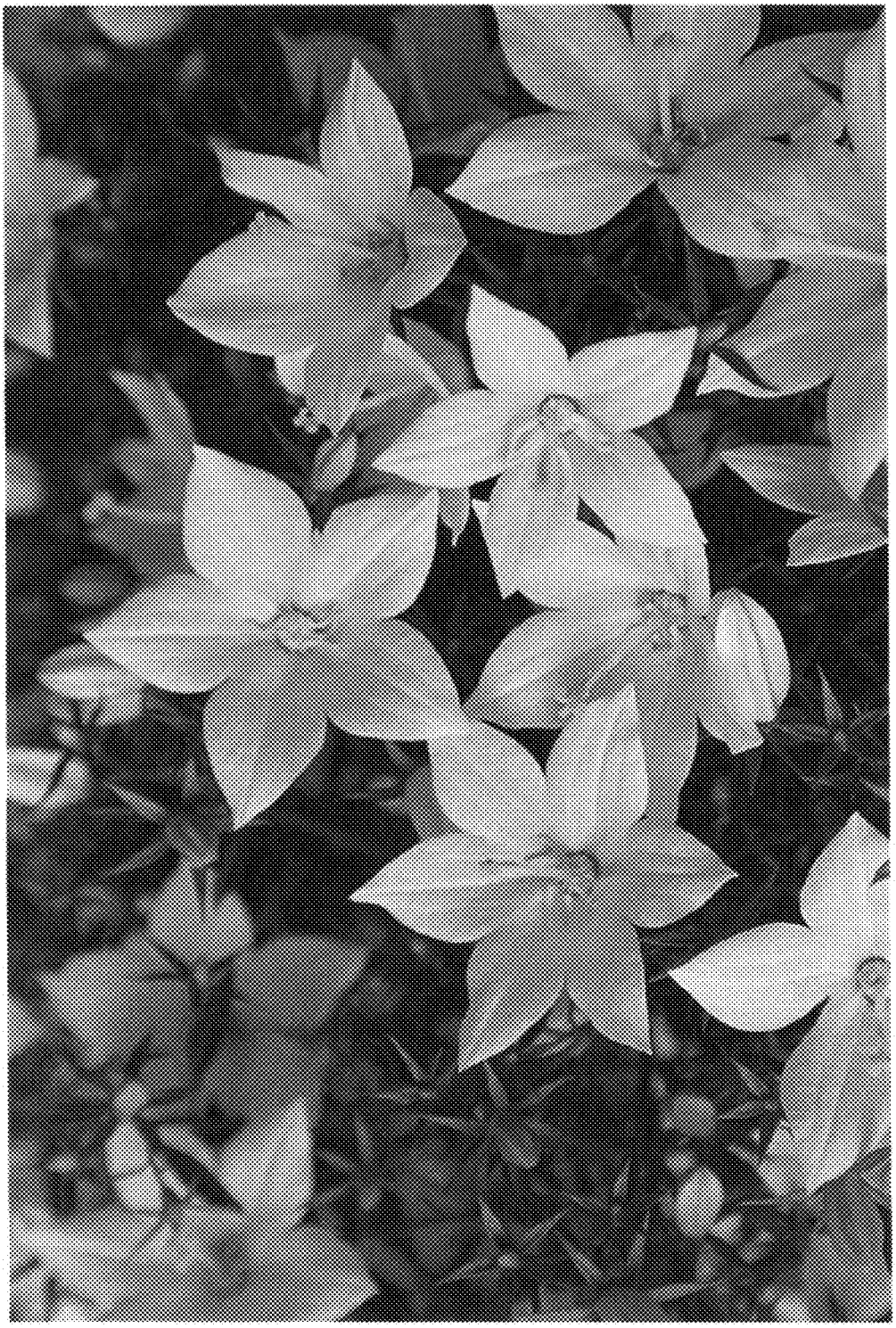

* * * * *